US00PP21521P2

(12) United States Plant Patent
Jepsen

(10) Patent No.: US PP21,521 P2
(45) Date of Patent: Nov. 23, 2010

(54) ***KALANCHOE* PLANT NAMED 'REESE'**

(50) Latin Name: *Kalanchoe blossfeldiana*
Varietal Denomination: Reese

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 12/459,836

(22) Filed: Jul. 8, 2009

(51) Int. Cl.
*A01H 5/00* (2006.01)

(52) U.S. Cl. ..... Plt./340

(58) Field of Classification Search ..... Plt./335, Plt./340, 341
See application file for complete search history.

*Primary Examiner*—June Hwu
(74) *Attorney, Agent, or Firm*—C. A. Whealy

(57) ABSTRACT

A new and distinct cultivar of *Kalanchoe* plant named 'Reese', characterized by its medium in size, upright, uniform and moderately vigorous growth habit; medium-sized to small dark green-colored leaves with crenate margins; uniform and freely flowering habit; medium-sized orange-colored flowers; and excellent postproduction longevity.

3 Drawing Sheets

Botanical designation: *Kalanchoe blossfeldiana.*
Cultivar denomination: 'Reese'.

BACKGROUND OF THE INVENTION

The present invention relates to a new and distinct cultivar of *Kalanchoe* plant, botanically known as *Kalanchoe blossfeldiana*, and hereinafter referred to by the name 'Reese'.

The new *Kalanchoe* plant is a naturally-occurring whole plant mutation of *Kalanchoe blossfeldiana* 'Sarah', disclosed in U.S. Plant Pat. No. 18,928. The new *Kalanchoe* was discovered and selected by the Inventor as a single flowering plant from within a population of plants of 'Sarah' in a controlled greenhouse environment in Hinnerup, Denmark in August, 2006.

Asexual reproduction of the new *Kalanchoe* plant by vegetative terminal cuttings in a controlled greenhouse environment in Hinnerup, Denmark since October, 2006, has shown that the unique features of this new *Kalanchoe* plant are stable and reproduced true to type in successive generations.

SUMMARY OF THE INVENTION

Plants of the new *Kalanchoe* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Reese'. These characteristics in combination distinguish 'Reese' as a new and distinct cultivar of *Kalanchoe:*

1. Medium in size, upright, uniform and moderately vigorous growth habit.
2. Medium-sized to small dark green-colored leaves with crenate margins.
3. Uniform and freely flowering habit.
4. Medium-sized orange-colored flowers.
5. Excellent postproduction longevity.

Plants of the new *Kalanchoe* can be compared to plants of the parent, 'Sarah'. Plants of the new *Kalanchoe* differ from plants of ' Sarah' primarily in flower color as plants of 'Sarah' have dark orange red-colored flowers.

Plants of the new *Kalanchoe* can be compared to plants of *Kalanchoe blossfeldiana* 'Carmen', disclosed in U.S. Plant Pat. No. 15,838. In side-by-side comparisons conducted in Hinnerup, Denmark, plants of the new *Kalanchoe* differed from plants of 'Carmen' in the following characteristics:

1. Plants of the new *Kalanchoe* had smaller vegetative leaves than plants of 'Carmen'.
2. Plants of the new *Kalanchoe* had smaller flowers than plants of 'Carmen'.
3. Flowers of plants of the new *Kalanchoe* were orange in color whereas flowers of plants of 'Carmen' were red orange in color.

BRIEF DESCRIPTION OF THE PHOTOGRAPHS

The accompanying colored photographs illustrate the overall appearance of the new *Kalanchoe*, showing the colors as true as it is reasonably possible to obtain in colored reproductions of this type. Colors in the photographs may differ slightly from the color values cited in the detailed botanical description which accurately describe the colors of the new *Kalanchoe.*

The photograph on the first sheet comprises a side perspective view of a typical flowering plant of 'Reese' grown in a container.

The photograph on the second sheet comprises a top perspective view of a typical flowering plant of 'Reese' grown in a container.

The photograph on the third sheet comprises close-up views of typical vegetative (bottom left) and generative (bottom right) leaves, side (center left) and top (center right) perspective views of typical flowers and a side perspective view of a typical flowering stem (top) of 'Reese'.

DETAILED BOTANICAL DESCRIPTION

The aforementioned photographs and following observations, measurements and values describe plants grown in Hinnerup, Denmark in a glass-covered greenhouse during the spring and under conditions which closely approximate commercial *Kalanchoe* production. During the production of the plants, day temperatures were averaged 19° C., night temperatures averaged 21° C. and light levels ranged from 10 kilolux to 50 kilolux. Unrooted cuttings were directly stuck in 10-cm containers and received long day/short night conditions (more than 14 hours of light) for about three weeks; plants then received photoinductive short day/long night conditions (minimum 14 hours darkness) until flowering. Plants were 13 weeks from planting when the photographs and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Reese'.

Parentage: Naturally-occurring whole plant mutation of *Kalanchoe blossfeldiana* 'Sarah', disclosed in U.S. Plant Pat. No. 18,928.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About three weeks at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit.; very freely flowering with numerous compound cymes; inverted triangle with rounded crown; appropriate for 9-cm and 10-cm containers.

*Plant height at flowering.*—About 20 cm to 27 cm.

*Plant diameter at flowering.*—About 22 cm.

*Branching habit.*—About six lateral branches develop per plant; pinching (removal of the terminal apex) is not required but will enhance lateral branch development.

Lateral branch description:

*Length.*—About 15 cm.

*Diameter.*—About 4 mm.

*Internode length.*—About 2 cm to 4 cm.

*Aspect.*—Erect.

*Strength.*—Strong.

*Texture.*—Smooth, glabrous.

*Color.*—Close to 147B.

Foliage description:

*Arrangement.*—Opposite, simple; generally symmetrical.

*Length, vegetative plants.*—About 8 cm to 11 cm.

*Width, vegetative plants.*—About 5 cm to 6 cm.

*Length, generative plants.*—About 3 cm to 11 cm.

*Width, generative plants.*—About 2 cm to 6 cm.

*Shape.*—Ovate.

*Apex.*—Obtuse to mucronate.

*Base.*—Cuneate.

*Margin.*—Crenate.

*Texture, upper and lower surfaces.*—Glabrous, leathery; succulent.

*Venation pattern.*—Pinnate.

*Color.*—Developing leaves, upper surface: Close to 137B. Developing leaves, lower surface: Close to 137C. Fully expanded leaves, upper surface: Close to 147A; venation, close to 146B. Fully expanded leaves, lower surface: Close to 146A; venation, close to 146B.

*Petiole.*—Length: About 5 mm to 10 mm. Diameter: About 5 mm to 6 mm. Texture, upper and lower surfaces: Smooth, glabrous. Color, upper and lower surfaces: Close to 137C.

Flower description:

*Flower arrangement and habit.*—Single flowers arranged in compound dichasial cymes that arise from leaf axils; uniform and freely flowering habit with usually about 40 to 80 flowers per inflorescence.

*Fragrance.*—Not detected.

*Natural flowering season.*—Plants of the new *Kalanchoe* flower from April to October when grown in an outdoor nursery. Flower initiation and development can also be induced under artificial short day/long night conditions (at least 14 hours of darkness) year-round in a greenhouse environment.

*Time to flower.*—Under short day/long night photoinductive conditions, about 74 days are required; actual time to flower is primarily dependent upon temperature and light intensity.

*Post-production longevity.*—Excellent post-production longevity; plants maintain good foliage and flower substance for about six weeks under interior environmental conditions; flowers not persistent.

*Inflorescence height.*—About 4 cm to 10 cm.

*Inflorescence diameter.*—About 5 cm to 9 cm.

*Flower diameter.*—About 1.6 cm.

*Flower length (height).*—About 1.8 cm.

*Flower bud.*—Shape: Lanceolate. Length: About 1.3 cm. Diameter: About 3 mm. Color: Initially close to 14A to 14B, with development, close to N30A.

*Petals.*—Arrangement: About four in a single whorl fused at the base. Length: About 1.8 cm. Width: About 6 mm. Aspect: Upright to eventually perpendicular to the pedicel. Shape: Rounded obovate. Apex: Apiculate. Margin: Entire. Texture, upper and lower surfaces: Smooth, glabrous. Color: When opening and fully opened, upper surface: Close to N25C; with development color becoming closer to 24A. When opening and fully opened, lower surface: Close to N30A and 23B; color does not fade with development.

*Sepals.*—Appearance: Four fused at the base. Length: About 9 mm. Width: About 2 mm. Shape: Lanceolate. Apex: Acute. Base: Truncate. Margin: Entire. Texture, upper and lower surfaces: Smooth; glabrous. Color, immature, upper and lower surfaces: Close to 146D. Color, mature, upper and lower surfaces: Close to 146C.

*Peduncles.*—Length: About 1 cm to 5 cm. Diameter: About 2 mm. Aspect: Erect to about 60° from vertical. Strength: Strong. Texture: Smooth, glabrous. Color: Close to 137C.

*Pedicels.*—Length: About 2 mm to 8 mm. Diameter: About 1 mm. Aspect: Erect to about 90° from vertical. Strength: Strong. Texture: Smooth, glabrous. Color: Close to 147B.

*Reproductive organs.*—Androecium: Stamen number: About eight per flower. Anther shape: Elliptic to oblong. Anther size: About 1 mm by 1 mm. Anther color: Close to 22B. Amount of pollen: Moderate. Pollen color: Close to 20A. Gynoecium: Pistil number: About four per flower. Pistil length: About 1.1 cm. Style length: About 2 mm. Style color: Close to N144A. Stigma shape: Round. Stigma color: Close to N144A. Ovary color: Close to 144C.

*Seed.*—Seed produced by plants of the new Kalanchoe typically do not mature and are not viable. Quantity per flower: About 40. Length: Less than 1 mm. Diameter: Less than 1 mm. Color, immature: Close to 145B.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Reese' as illustrated and described.

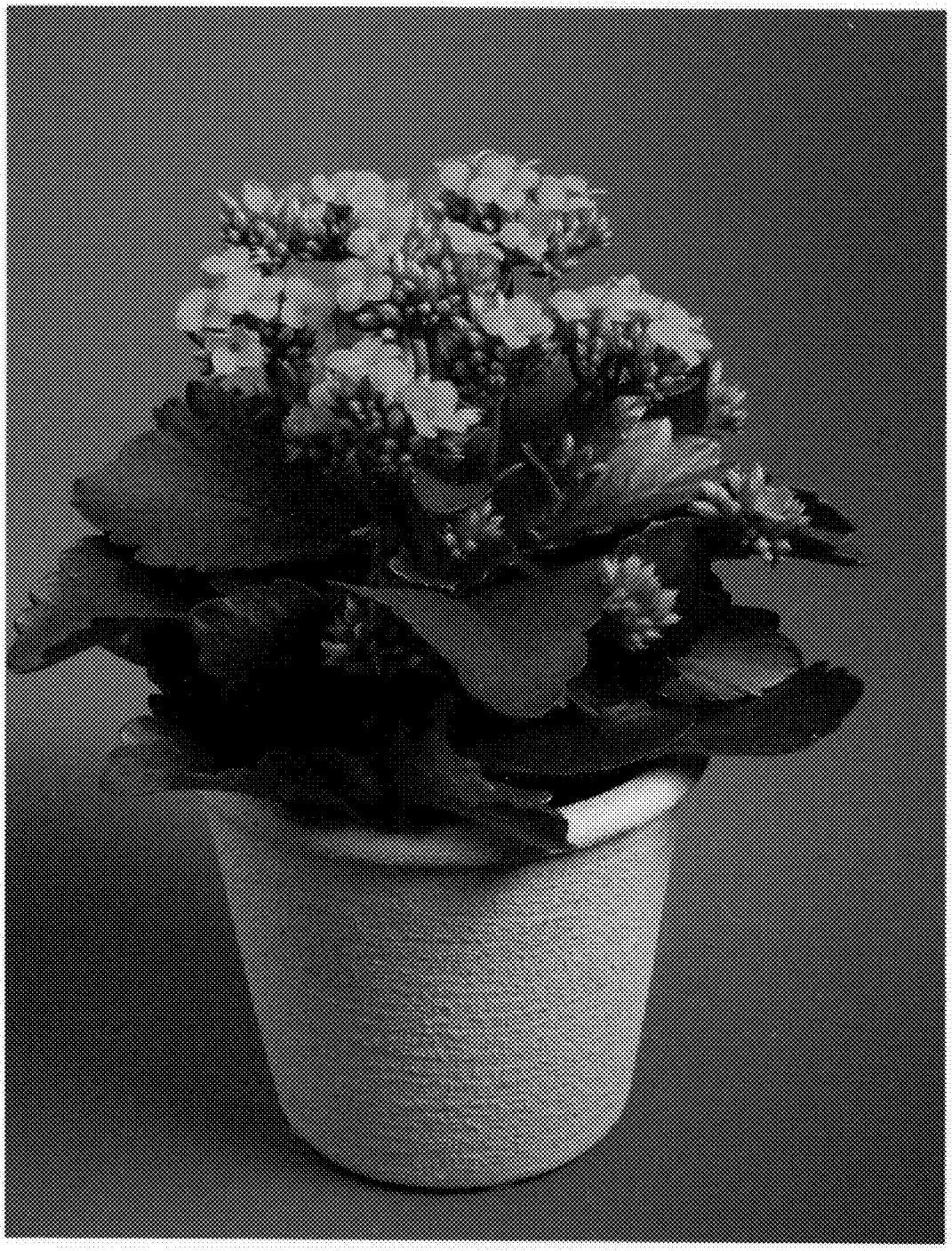

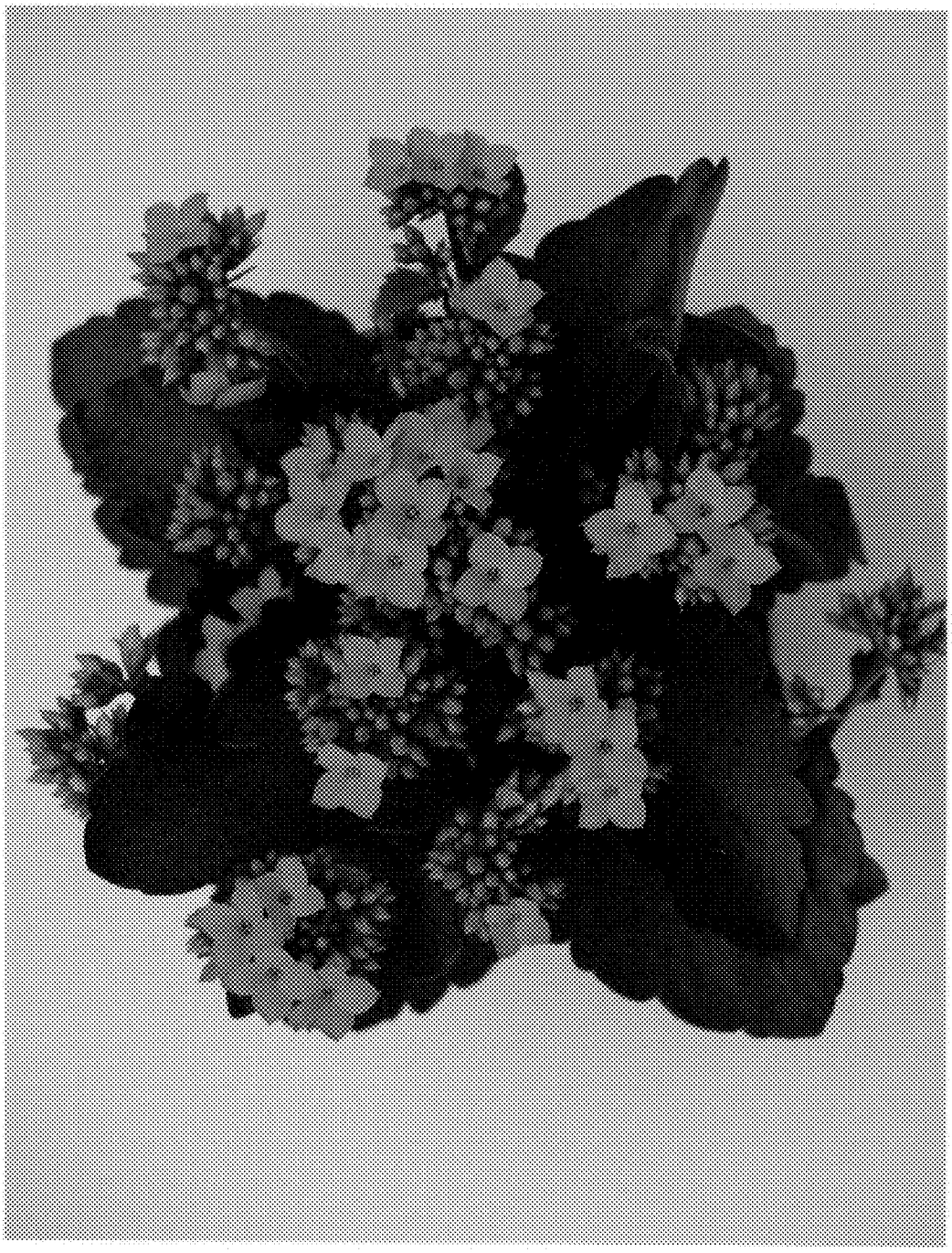

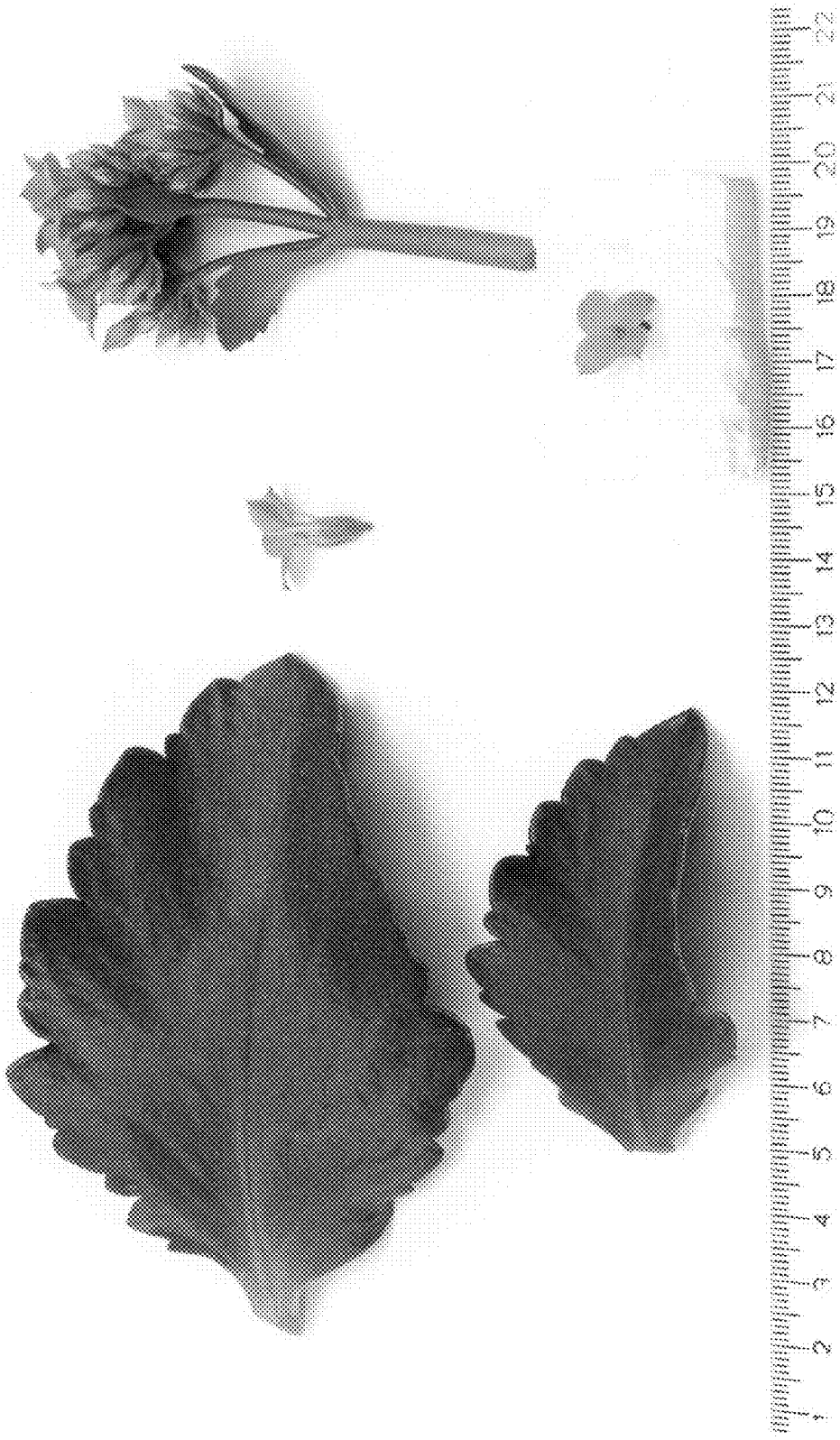

* * * * *